US010080554B2

(12) United States Patent
Hamel et al.

(10) Patent No.: US 10,080,554 B2
(45) Date of Patent: *Sep. 25, 2018

(54) FOOT-OPERATED CONTROL CONSOLE FOR WIRELESSLY CONTROLLING MEDICAL DEVICES

(71) Applicants: Andrew J. Hamel, Portola Valley, CA (US); Michael D. Baycura, San Francisco, CA (US); Michael G. Hilldoerfer, San Jose, CA (US); Vasudev Nambakam, San Jose, CA (US); Salmaan Hameed, San Jose, CA (US); William H. L. Chang, Milpitas, CA (US)

(72) Inventors: Andrew J. Hamel, Portola Valley, CA (US); Michael D. Baycura, San Francisco, CA (US); Michael G. Hilldoerfer, San Jose, CA (US); Vasudev Nambakam, San Jose, CA (US); Salmaan Hameed, San Jose, CA (US); William H. L. Chang, Milpitas, CA (US)

(73) Assignee: STRYKER CORPORATION, Kalamazoo, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 15/618,861

(22) Filed: Jun. 9, 2017

(65) Prior Publication Data

US 2017/0273673 A1 Sep. 28, 2017

Related U.S. Application Data

(60) Continuation of application No. 14/688,188, filed on Apr. 16, 2015, now Pat. No. 9,681,858, which is a
(Continued)

(51) Int. Cl.
*A61B 17/00* (2006.01)
*G08C 17/02* (2006.01)
(Continued)

(52) U.S. Cl.
CPC ........ *A61B 17/00* (2013.01); *A61B 17/32002* (2013.01); *A61B 90/70* (2016.02);
(Continued)

(58) Field of Classification Search
CPC .............. A61B 17/00; A61B 17/32002; A61B 18/1482; A61B 2017/00017;
(Continued)

(56) References Cited

U.S. PATENT DOCUMENTS 4,513,284 A 4/1985 Right
4,670,747 A 6/1987 Borras et al.
(Continued)

FOREIGN PATENT DOCUMENTS

CA 2 353 016 A1 1/2002
EP 1 629 786 A2 3/2006
(Continued)

OTHER PUBLICATIONS

Dawn Etta, "Customized Foot Switches for Medical Applications," Medical Equipment Designer, pp. 1-6, Nov. 1998, downloaded from http://www.manufacturingcenter.com/med/archives/1198/1198foot.asp, Apr. 14, 2003.
(Continued)

*Primary Examiner* — Yong Hang Jiang
(74) *Attorney, Agent, or Firm* — Flynn Thiel, P.C.

(57) ABSTRACT

A wireless foot control apparatus allows an operator to control multiple medical devices during an endoscopic medical procedure. The apparatus comprises a control console with controls designed for foot operation to control various medical devices. The controls include one or more
(Continued)

foot pedals and foot switches to control the devices, including a selection switch to allow selection of the device to be controlled at a particular time. The console transmits signals over a wireless medium, to cause a remote receiver unit to select the device to be controlled and to control the selected device over a wired medium, in response to operation of the foot controls. The console may include a rechargeable battery, which may be sealed within the console's housing and charged inductively when the console is placed in a charging station. The receiver unit and the charging station can be separate units or integrated within a single housing.

31 Claims, 15 Drawing Sheets

Related U.S. Application Data division of application No. 10/607,810, filed on Jun. 27, 2003, now Pat. No. 9,035,741.

(51) Int. Cl.
   *A61B 17/32* (2006.01)
   *A61B 90/70* (2016.01)
   *A61B 18/14* (2006.01)

(52) U.S. Cl.
   CPC .......... *G08C 17/02* (2013.01); *A61B 18/1482* (2013.01); *A61B 2017/00017* (2013.01); *A61B 2017/00199* (2013.01); *A61B 2017/00734* (2013.01); *A61B 2017/00973* (2013.01); *A61B 2090/701* (2016.02); *G08C 2201/70* (2013.01)

(58) Field of Classification Search
   CPC .......... A61B 2017/00199; A61B 2017/00734; A61B 2017/00973; A61B 2090/701; A61B 90/70; G08C 17/02; G08C 2201/70
   See application file for complete search history.

(56) References Cited

U.S. PATENT DOCUMENTS

| | | | |
|---|---|---|---|
| 5,046,107 A | 9/1991 | Iwamatsu | |
| 5,223,826 A | 6/1993 | Amou et al. | |
| 5,336,218 A | 8/1994 | Linhares | |
| 5,422,521 A | 6/1995 | Neer et al. | |
| 5,524,180 A | 6/1996 | Wang et al. | |
| 5,635,777 A | 6/1997 | Telymonde et al. | |
| 5,734,254 A | 3/1998 | Stephens | |
| 5,790,065 A | 8/1998 | Yaroch | |
| 5,883,615 A | 3/1999 | Fago et al. | |
| 5,904,681 A | 5/1999 | West, Jr. | |
| 5,910,139 A | 6/1999 | Cochran et al. | |
| 6,040,680 A | 3/2000 | Toya et al. | |
| 6,043,626 A | 3/2000 | Snyder | |
| 6,074,388 A | 6/2000 | Tockweiler et al. | |
| 6,359,348 B1 | 3/2002 | King | |
| 6,451,017 B1 | 9/2002 | Moutafis et al. | |
| 6,504,117 B2 | 1/2003 | Overstreet | |
| 6,511,493 B1 | 1/2003 | Moutatis et al. | |
| 6,646,541 B1 | 11/2003 | Wang et al. | |
| 6,679,875 B2 | 1/2004 | Honda et al. | |
| 6,716,219 B1 | 4/2004 | Koch | |
| 6,853,308 B1 | 2/2005 | Dustin | |
| 6,926,130 B2 | 8/2005 | Skowronski | |
| 7,217,269 B2 | 5/2007 | El-Galley et al. | |
| 7,228,190 B2 | 6/2007 | Dowling et al. | |
| 7,353,068 B2 | 4/2008 | Tanaka et al. | |
| 7,366,934 B1 | 4/2008 | Narayan et al. | |
| 7,660,420 B1 | 2/2010 | Narayan et al. | |
| 7,752,050 B1 | 7/2010 | Hameed et al. | |
| 7,846,150 B2 | 12/2010 | Hamel et al. | |
| 2001/0007815 A1 | 7/2001 | Philipsson | |
| 2001/0029315 A1 | 10/2001 | Sakurai et al. | |
| 2001/0051802 A1 | 12/2001 | Woloszko et al. | |
| 2002/0087179 A1 | 7/2002 | Culp et al. | |
| 2002/0128846 A1 | 9/2002 | Miller | |
| 2002/0156466 A1 | 10/2002 | Sakurai et al. | |
| 2003/0050009 A1* | 3/2003 | Kurisko | H04L 63/061 455/41.1 |
| 2003/0060818 A1 | 3/2003 | Kannenberg et al. | |
| 2003/0073980 A1 | 4/2003 | Finlay et al. | |
| 2003/0093503 A1 | 5/2003 | Yamaki et al. | |
| 2003/0225403 A1 | 12/2003 | Woloszko et al. | |
| 2004/0172011 A1 | 9/2004 | Wang et al. | |
| 2005/0049458 A1 | 3/2005 | Honda et al. | |
| 2005/0080403 A1 | 4/2005 | Takahashi | |
| 2005/0143724 A1 | 6/2005 | El-Galley et al. | |
| 2005/0251228 A1 | 11/2005 | Hamel | |
| 2006/0047100 A1 | 3/2006 | Murouchi et al. | |
| 2006/0047199 A1 | 3/2006 | Miyazawa | |
| 2006/0116667 A1 | 6/2006 | Hamel et al. | |
| 2008/0140158 A1 | 6/2008 | Hamel et al. | |
| 2009/0121865 A1 | 5/2009 | Hamel et al. | |
| 2015/0216513 A1 | 8/2015 | Hamel et al. | |

FOREIGN PATENT DOCUMENTS

| | | |
|---|---|---|
| JP | 11-318916 A | 11/1999 |
| WO | WO 2008/098085 A2 | 8/2008 |

OTHER PUBLICATIONS

"New features from steute," steute Meditech, pp. 1-3, downloaded from http://www.steute.com/cms1/opencms/html/medizin/en/produkte/produktneuheiten.html?id=2, Apr. 14, 2003.

"HERMES™ Operating Room Control Center, Operating & Maintenance Manual," Stryker® Endoscopy, May 1999.

"FDA Approval of Additional Devices for Computer Motion's HERMES Control Center", Medical Robotics Updates, TeleMed-E-Zine, Jul. 1999, vol. 2 Issue 7.

Karl Storz Communication Bus (SCB), EndoWorld, Nov. 1999.

* cited by examiner

FOOT-OPERATED CONTROL CONSOLE FOR WIRELESSLY CONTROLLING MEDICAL DEVICES

CROSS REFERENCE TO RELATED APPLICATIONS

This is a continuation of prior U.S. application Ser. No. 14/688,188, filed Apr. 16, 2015, which is a divisional of prior U.S. application Ser. No. 10/607,810, filed Jun. 27, 2003, which issued as U.S. Pat. No. 9,035,741, all of which are hereby incorporated by reference in their entirety.

FIELD OF THE INVENTION

At least one embodiment of the present invention pertains to foot-operated control devices, and more particularly, to a foot-operated control console to control multiple medical devices wirelessly during an endoscopic surgical procedure.

BACKGROUND

Endoscopy is a technology that allows minimally-invasive viewing of internal features of a body. In medicine, endoscopy allows acquisition of high-quality images of internal features of a human body without the need for invasive surgery. The basic tool of endoscopy is the endoscope ("scope"), which is inserted into the body to be viewed. Some endoscopic procedures involve the use of a flexible scope, as in the medical field of gastroenterology, for example. Other medical procedures, such as arthroscopy or laparoscopy, use a rigid scope. The scope is normally coupled to a high-intensity light source that transmits light into the body through the scope, and to a camera head that includes electronics for acquiring video image data. The camera head is typically coupled to a video monitor, which displays video images acquired by the camera.

In endoscopic surgery, various other medical devices may be used, such as an insufflator to pump pressurized gas into body cavities to create more space for viewing and working, an electrocautery tool to stop bleeding, and/or various tools to cut or shape body tissues. These devices are typically controlled by foot pedals and/or switches placed on the floor of the operating room, which are operated by the surgeon. The foot controls may control functions such as on/off, speed or intensity, direction of movement of the tool, mode of operation, etc. The use of foot controls, rather than hand-operated controls, allows the surgeon to adjust various modes and settings of the tools (e.g., speed, intensity) himself, without having to put a tool down, change hands, touch potentially contaminated surfaces with his hands, or take his eyes off the patient.

In the known prior art, foot-operated medical devices such as those mentioned above each have their own separate, dedicated foot controls, resulting in the presence of multiple foot controls in the operating room. The presence of multiple foot controls in the operating room can result in confusion about which foot control operates a particular device. Furthermore, the cables that connect the foot controls to their respective devices can create a safety hazard and a nuisance, since operating room personnel may trip over them and the cables may become tangled.

BRIEF DESCRIPTION OF THE DRAWINGS

One or more embodiments of the present invention are illustrated by way of example and not limitation in the figures of the accompanying drawings, in which like references indicate similar elements and in which.

DETAILED DESCRIPTION

A wireless foot control apparatus to allow an operator to control multiple medical devices during a medical procedure is described. Note that in this description, references to "one embodiment" or "an embodiment" mean that the feature being referred to is included in at least one embodiment of the present invention. Further, separate references to "one embodiment" or "an embodiment" in this description do not necessarily refer to the same embodiment; however, such embodiments are also not mutually exclusive unless so stated, and except as will be readily apparent to those skilled in the art from the description. For example, a feature, structure, act, etc. described in one embodiment may also be included in other embodiments. Thus, the present invention can include a variety of combinations and/or integrations of the embodiments described herein.

As described in greater detail below, a single wireless foot control console in accordance with the invention allows a surgeon or other operator to control multiple medical devices during an endoscopic medical procedure. The console comprises multiple controls designed for operation by an operator's foot to control the medical devices, including one or more foot pedals and/or foot switches to control the devices, including a selection switch to allow selection of the device to be controlled. In response to operation of the foot controls, the console transmits signals wirelessly to a receiver unit, which causes the receiver unit to select a device to be controlled and to control the selected device. The foot control console may include a rechargeable battery, which may be sealed within the console's housing and charged inductively when the console is placed in a docking station. The receiver unit and the docking station can be separate units or they can be integrated within a single housing.

Figure 1:
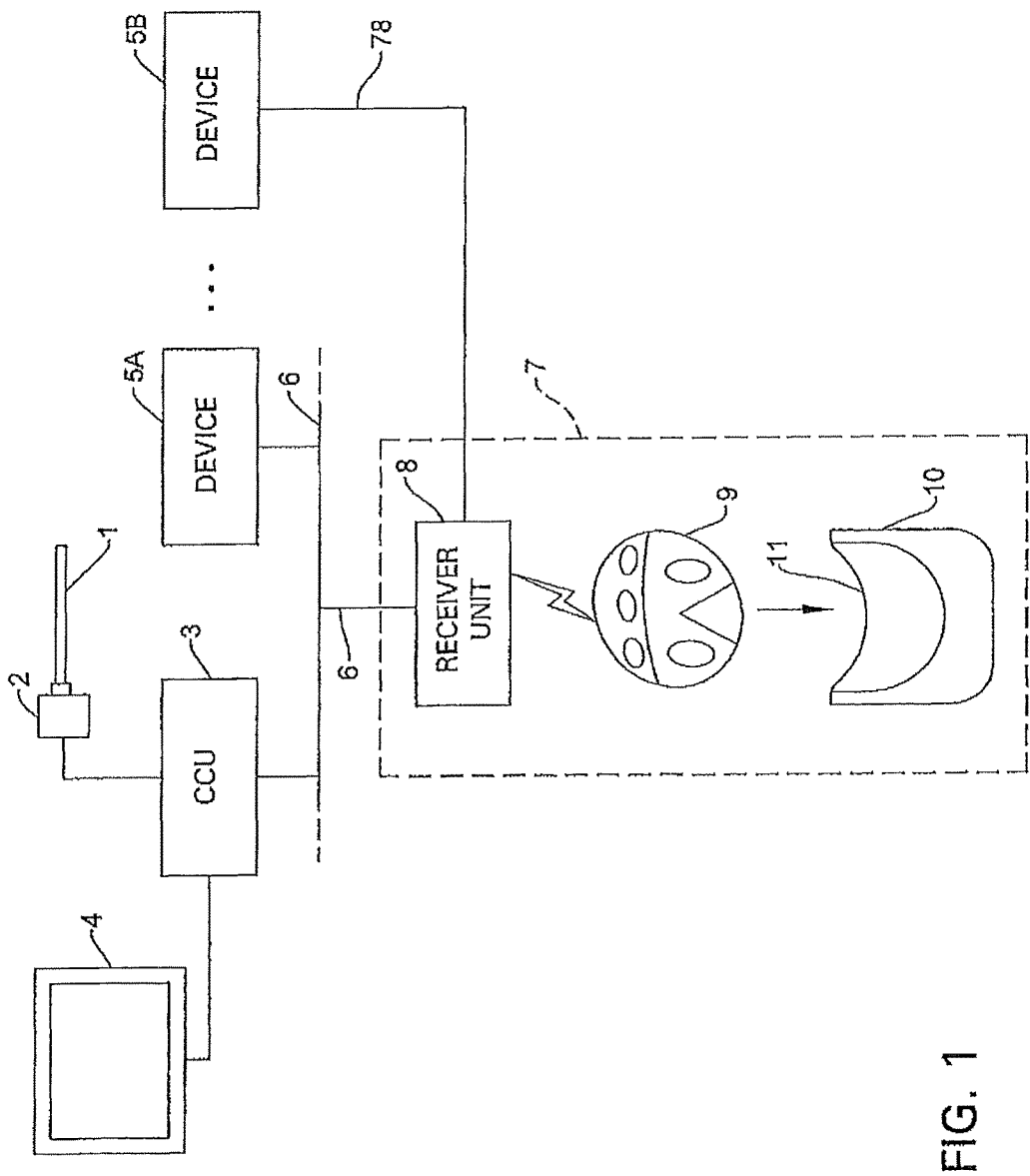
FIG. 1 is a block diagram of a medical endoscopy system including a wireless foot control apparatus according to certain embodiments of the invention.

FIG. 1 shows a medical endoscopy system that includes a wireless foot control apparatus according to the invention. The system includes an endoscope 1 and a camera 2 coupled to the endoscope 1 and to a camera control unit (CCU) 3. Also coupled to the CCU 3 is a video monitor 4 to display images acquired by the camera 2. The system also includes a number of different supporting devices 5 (e.g., 5A, 5B, etc.), which may include, for example, an insufflator, an electrocautery tool, a radio frequency (RF) generator, a cutter/shaver tool, and/or other devices. One or more of these supporting devices 5 may be connected to each other by a common wired communication medium 6, as are device 5A and the CCU 3. The wired communication medium 6 may be, for example, an IEEE standard 1394 backplane connection, an Ethernet connection, or other communication medium with similar capability.

Also connected to the wired communication medium 6 is a receiver unit 8, which is an element of a wireless foot control apparatus 7 in accordance with the invention. The other elements of the wireless foot control apparatus 7 are a foot-operated control console 9 and a docking station 10. The console 9 and receiver unit 8 cooperate to allow the operator to control any of the devices 5. Specifically, the console 9 includes various foot operated pedals, switches and/or other foot-operated controls which, when actuated by the operator, cause the console 9 to transmit control signals wirelessly to the receiver unit 8. In response to control signals received from the console 9, the receiver unit 8 communicates with the currently selected one of the various devices 5. This communication may occur over the wired communication medium 6, as would be the case with device 5A. However, one or more of the controlled devices 5 might not be connected to the wired communication medium 6, such as device 5B. Such devices 5 may instead have a direct connection 78 (which may be analog or digital) to the receiver unit 8. The direct connection 78 may emulate the inputs of a device-specific footswitch to the device 5. Furthermore, one or more controlled devices 5 might communicate with the receiver unit 8 only via a wireless link.

In some embodiments, a receiver may be built into the controlled device 5 itself, such that a dedicated receiver unit 8 and any wired connections between the receiver and the device would be unnecessary.

In the illustrated embodiment, the docking station 10 is used to charge a rechargeable battery (not shown) within the console 9. The docking station 10 includes a receptacle 11 designed to accommodate the console 9 and includes a power supply and circuitry (not shown) used to charge the battery in the console 9. The docking station 10 can be conveniently placed or mounted on an equipment cart, a table, the operating room floor, or a wall.

In alternative embodiments, the receiver unit 8 can be contained within the docking station 10. Also, in alternative embodiments, the battery can be removed from the console 9 and placed in its own dedicated charger for recharging, such that no docking station 10 is required, as described further below. Also, in alternative embodiments, the battery could be a standard alkaline battery and require no charging station at all, but simply be replaced in the console as needed.

Figure 2:
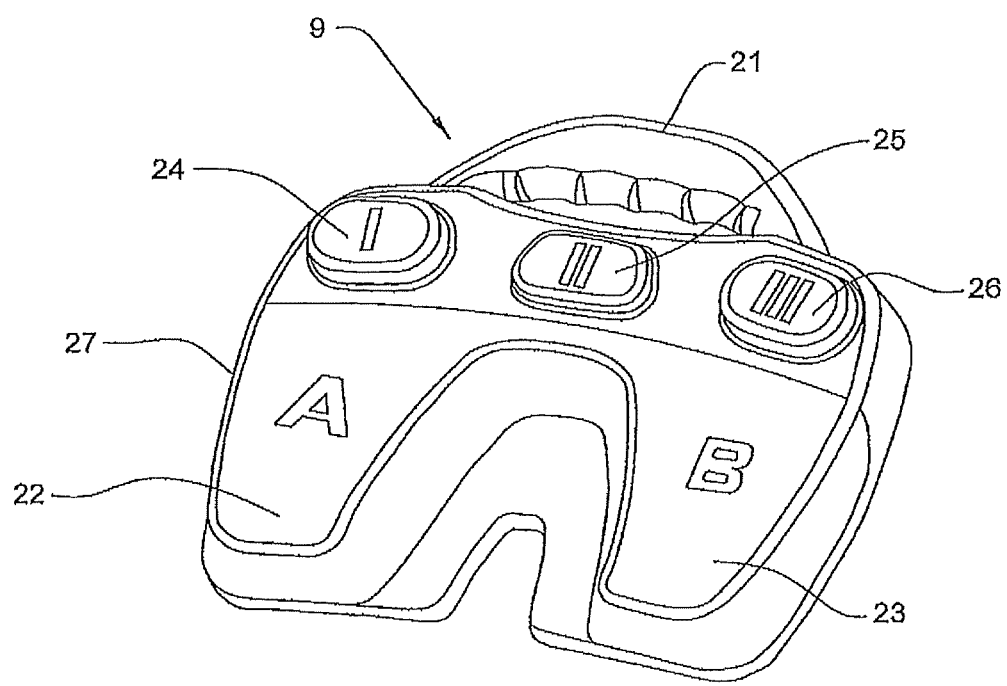
FIG. 2 shows an exterior view of the foot control console according to certain embodiments of the invention.

FIG. 2 shows an exterior view of the console 9 according to certain embodiments of the invention. The console 9 is relatively light in weight and includes a handle 21 that allows the console 9 to be conveniently picked up and carried by operating room staff. As shown, the console 9 includes a left and right pedals 22 and 23, respectively, as well as three foot operated switches, i.e., a left switch 24, a middle switch 25, and a right switch 26. Other embodiments may include a different combination of pedals, switches, and/or other controls. The switches 24-26 may be, for example, simple pushbutton switches and may be used, for example, to select different modes of operation of the various devices 5. The pedals 22 and 23 may be simple potentiometer-type (variable displacement) foot controls, such as for use in controlling the speed, intensity, and/or other variable settings of a medical tool.

In certain embodiments, the console 9, while capable of controlling any of the devices 5, controls only one of the devices 5 at a time. In such embodiments, one of the switches 24-26 is used as a selection switch to allow the operator to select the device 5 to be controlled. The function of each of the other controls can vary depending upon which device 5 is currently selected to be controlled. The selection can be accomplished by simply pressing the designated selection switch repeatedly to cycle between the different available devices 5.

In other embodiments, the console 9 is capable of controlling two or more devices 5 simultaneously. For example, two or more separate switches and/or pedals can be used to control two or more separate devices 5 at the same time. Or, the same control on the console 9 might be used to control two or more devices.

The receiver 8 will detect which devices are present or connected to the wired communication medium 6 and/or the direct connection 78. Therefore, the console 9 does not need to have any knowledge of which device 5 is currently selected—such knowledge can be maintained entirely within the receiver unit 8. The console 9 simply transmits generic control signals, which the receiver unit 8 translates the control signals into other control signals in the appropriate format and protocol for the currently selected device 5. In some embodiments, the receiver 8 can receive input from multiple consoles 9 simultaneously and output the corresponding control signal to either one or multiple devices, depending on if the multiple consoles are controlling the same device or multiple devices.

As discussed above, in certain embodiments the console 9 has its own internal power supply, which may be a rechargeable battery (or multiple batteries) sealed within the housing 27 of the console 9. In such embodiments, the housing 27 can be made of molded plastic or other similar material, making the console 9 lightweight, durable, soakable, and easy to clean. This approach is desirable because, among other reasons, it is common during certain endoscopic surgical procedures for considerable amounts of water and/or other fluids to be spilled onto the floor of the operating room. A sealed console housing is advantageous, therefore, since there is no need for electrical contacts that are directly exposed to this operating room environment. In addition, the use of a rechargeable internal battery reduces the number of electrical cables needed in the operating room.

Figure 3:
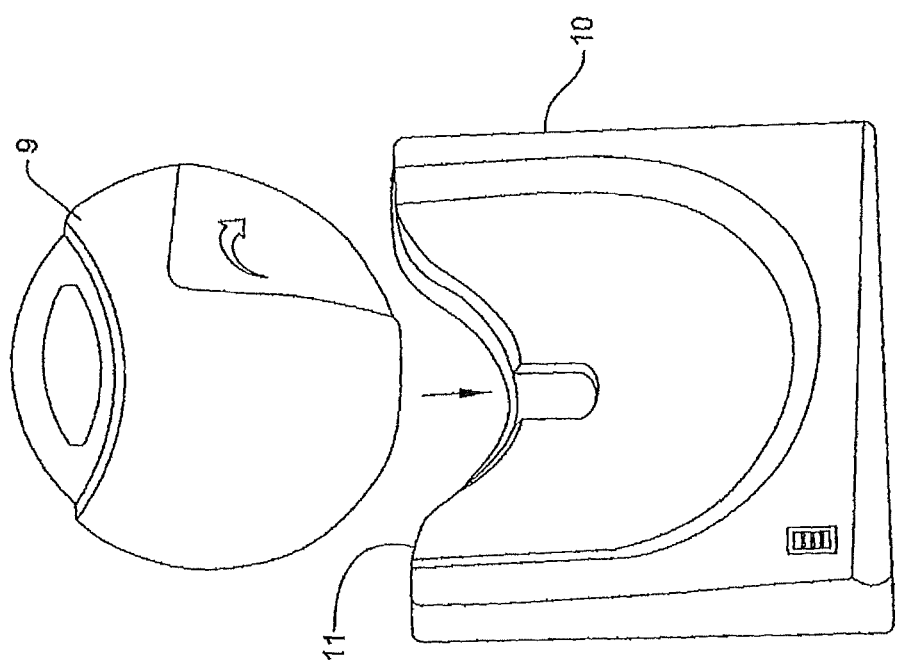
FIG. 3 shows the wireless foot control console and a docking station into which the console can be placed to recharge a battery in the wireless foot control apparatus.
Figure 4:
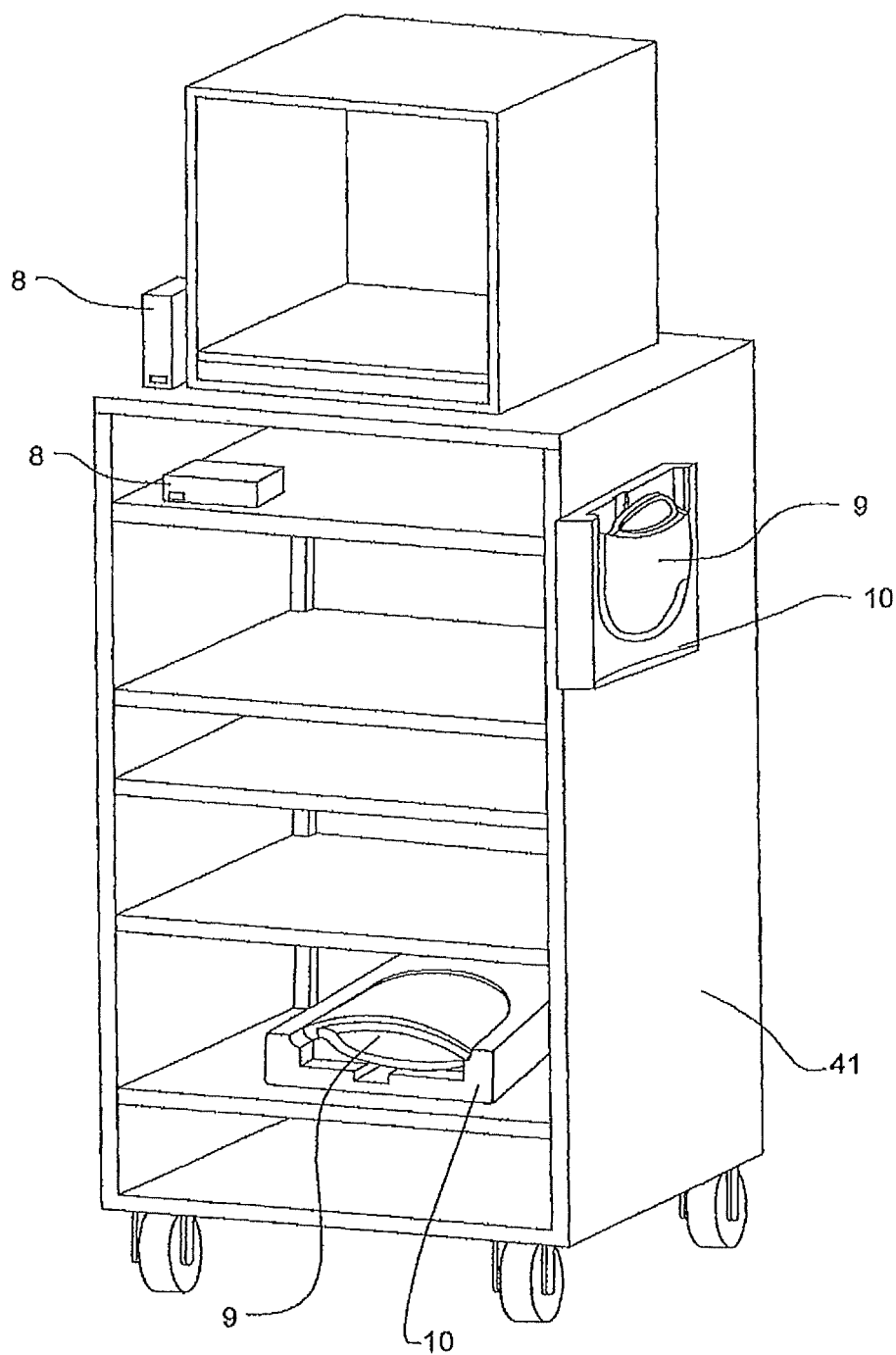
FIG. 4 shows how the docking station and the receiver unit can be placed or mounted on an equipment cart.

To charge the internal battery, the console 9 is placed into the docking station 10, where the battery is charged by electromagnetic induction. The docking station 10 also serves as a convenient holder for the console 9 when the console 9 is not in use. FIG. 3 shows how the console 9 is inserted into the docking station 10 for charging of the console's battery and/or for storage. FIG. 4 shows how a docking station 10 can be placed or mounted on an equipment cart 41 of the type typically used for endoscopic equipment.

Figure 5:
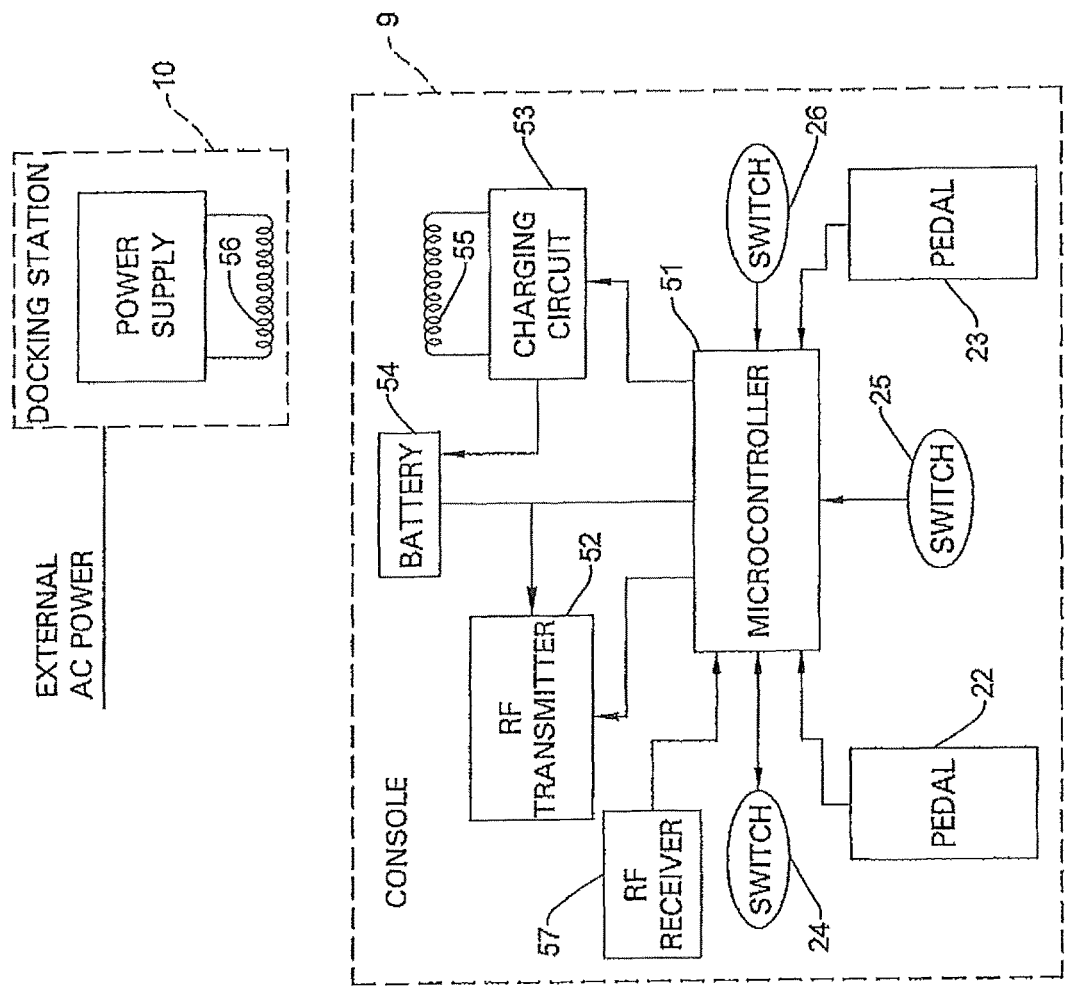
FIG. 5 is a block diagram of the console according to certain embodiments of the invention.

FIG. 5 shows the components of a console 9, according to certain embodiments of the invention. As illustrated, the console 9 includes a conventional programmable microcontroller 51. The console 9 also includes a relatively short-range radio frequency (RF) transmitter 52 and a charging circuit 53, each coupled to the microcontroller 51. The console 9 further includes at least one rechargeable battery 54 and an induction coil 55 coupled to the charging circuit 53. The internal components of the console 9 (i.e., other than the switches and pedals) are completely sealed within the housing of the console 9, which protects those components from damage from the operating room environment and reduces the risk of electrical shock and sparks.

The microcontroller 51 is primarily responsible for identifying the source of each particular user input (i.e., which specific switch or pedal) but may also perform various other control functions such as described herein. The microcontroller 51 may, in other embodiments, be replaced by one or more other forms of control device capable of performing the same role, such as a programmable general-purpose or special-purpose microprocessor, application specific integrated circuit (ASIC), etc. (i.e., from which switch or pedal).

The microcontroller 51 can communicate with the RF transmitter 52 through a standard RS-232 interface, for example. The RF transmitter 52 transmits control signals to the receiver unit 8, under the control of the microcontroller 51, in response to user inputs applied at the foot operated controls (switches and pedals). The RF transmitter 52 may be, for example, a conventional Bluetooth transmitter. In other embodiments, the RF transmitter 52 may operate in accordance with any one or more wireless communication standards, such as wireless Ethernet, IEEE standards 802.11a, 802.11b and 802.11g, 802.12 and 802.16. Furthermore, in other embodiments, the console 9 can communicate with the receiver unit 8 using a form of wireless communication other than RF, such as infrared (IR), laser, etc.

In alternative embodiments, each control on the console 9 may have its own RF transmitter in the console 9, to communicate with the receiver unit 8, such that no central microcontroller is needed to identify the source of each user input.

The console 9 may also include an RF receiver 57 coupled to the microcontroller 51, which can be used to receive data from the receiver unit 8 or another device for various purposes, such as modifying various parameters or settings of the console 9. The receiver 57 may be, for example, a conventional Bluetooth receiver. Note that the RF receiver 57 and transmitter 52 may be combined in a single transceiver.

The induction coil 55 and charging circuit 53 are used to recharge the battery 54 while the console 9 is situated in the docking station 10 (while the docking station 10 is powered). The battery 54 may be, for example, a NiMH or Li+ battery. The charging circuit 53 controls charging of the battery 54 using power induced in the secondary induction coil 55 by a corresponding primary induction coil 56 within the docking station 10. The console 9 and docking station 10 are designed so that the induction coil 55 in the console 9 and the induction coil 56 in the docking station 10 are positioned in close proximity to each other when the console 9 is placed in the docking station 10, although they are separated by the housings of the console 9 and the docking station 10. As shown, the docking station 10 can include simply a regulated power supply 76 coupled to the primary induction coil 56, both contained within a housing that has a receptacle 11 (FIGS. 1 and 3) shaped to accommodate the console 9 as described above.

Figure 6:
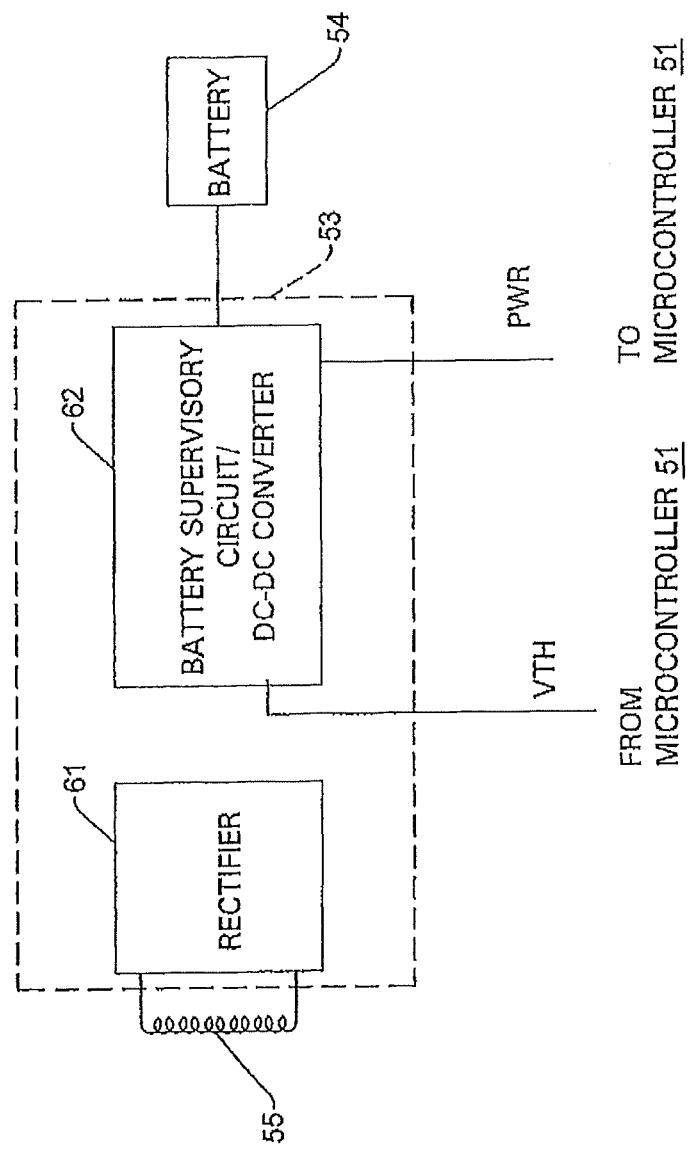
FIG. 6 shows the charging circuit in the console according to certain embodiments of the invention.

FIG. 6 shows the charging circuit 55 in greater detail. As shown, the charging circuit 53 includes a rectifier 61 coupled to the terminals of the secondary induction coil 55, and a battery supervisory circuit/DC-DC converter 62. The battery 54 is coupled to the secondary induction coil 55 via the rectifier 61 and the battery supervisory circuit/DC-DC converter 62. The battery supervisory circuit DC-DC converter 62 receives from the microcontroller 51 an input voltage $V_{TH}$. When the input voltage $V_{TH}$ is present and the console 9 is docked within the docking station 10, the battery supervisory circuit DC-DC converter 62 charges the battery. When not docked, the battery supervisory circuit DC-DC converter 62 provides regulated power PWR to the microcontroller 51. Circuits and techniques for charging a rechargeable power supply inductively are further described in various sources, such as in U.S. Pat. No. 6,040,680 of Toya et al.

Figure 7A:
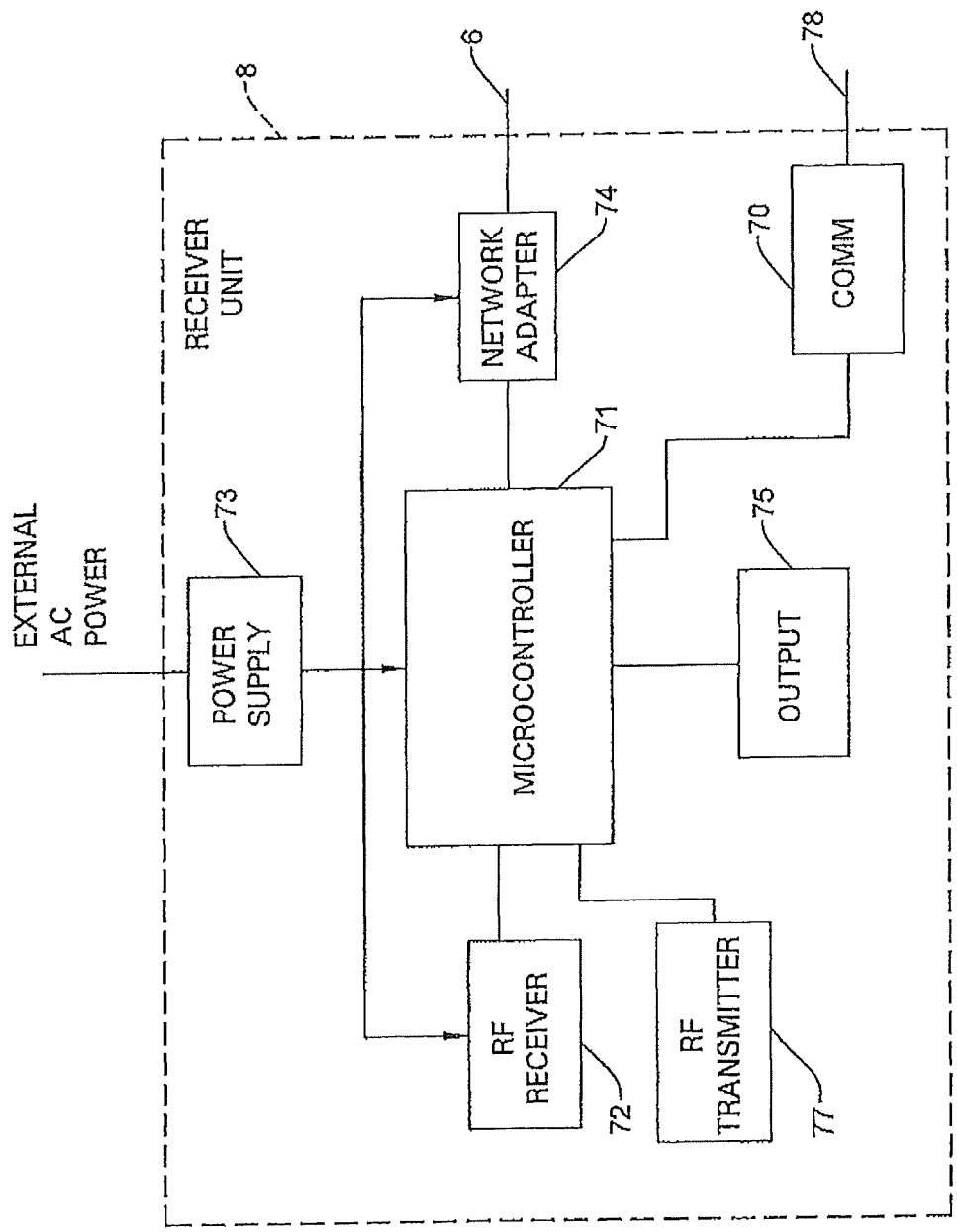
FIG. 7A is a block diagram of the receiver unit, according to certain embodiments of the invention.

FIG. 7A is a block diagram of the receiver unit 8, according to certain embodiments of the invention. As shown, the receiver unit 8 includes a programmable microcontroller 71, a wireless receiver 72, a power supply 73, a network adapter 74, and one or more output indicators 75. The microcontroller 71 controls the overall operation of the receiver unit 8. The microcontroller 71 may, in other embodiments, be replaced by one or more other forms of control device capable of performing the same role, such as a programmable general-purpose or special-purpose microprocessor, ASIC, etc. The wireless receiver 72 receives control signals transmitted from the console 9 as described above. The microcontroller 71 may communicate with the RF transmitter 72 through a standard RS-232 interface, for example. The power supply 73 provides regulated power for the receiver unit 8, based on power supplied from any available external power source.

The output indicator(s) 75 are used to communicate various information to the user, including to indicate which device 5 (FIG. 1) is currently selected. The output indicator(s) 75 may include, for example, one or more light-emitting diodes (LEDs), liquid crystal displays (LCDs), audio speakers, or the like.

Depending upon which of the devices 5 is currently selected, the microcontroller 71 uses the control signals received by the wireless receiver 72 to generate commands and/or other control signals directed to a particular device 5 on the wired communication medium 6. The microcontroller 71 is programmed to generate specific commands or other control signals in a format and/or protocol that is appropriate for the currently selected device 5. The microcontroller 71 causes the network adapter 74 to transmit these generated commands onto the wired communication medium 6.

The network adapter 74 may be, for example, a standard IEEE standard 1394 adapter, for example, where the wired communication medium 6 is an IEEE 1394 backplane. In that case, the receiver unit 8 can use standard IEEE 1394 protocols to identify the other devices that are connected to the backplane. In still other embodiments, a communication medium other than an IEEE 1394 backplane may be used.

In certain embodiments, the receiver unit 8 also (or instead) can have one or more "direct" (i.e., non-network) connections 78 to a controlled device 5, as mentioned above and as shown in FIG. 1. In such embodiments, the receiver unit 8 includes a communication adapter 70 to couple the microcontroller 71 to the direct connection 78. In certain instances, a direct connection 78 may be implemented as a connection between the receiver unit 9 and a device 5 with no other devices or adapters coupled between them, while in other cases, a direct connection 78 may be implemented by connecting the receiver unit 9 to a device 5 through a separate, external adapter ("dongle") that emulates the network connection for the receiver unit 8.

The receiver unit 8 may also include an RF transmitter 77, to transmit data to the console 9 as described above. Note that the RF receiver 72 and transmitter 77 may be combined in a single transceiver.

In the embodiments described above, the receiver unit 8 and the docking station 10 are separate, stand-alone units. In alternative embodiments, however, the receiver unit 8 may be integrated within the housing of the docking station 10. In such embodiments, the internal elements of such a combined unit are essentially the combination of the elements of the docking station 10, such as shown in FIG. 5, and the elements of the receiver unit 8, such as shown in FIG. 7A. Also, as mentioned above, the receiver unit 8 could be replaced by a receiver internal to the device 5 to be controlled.

Figure 7B:
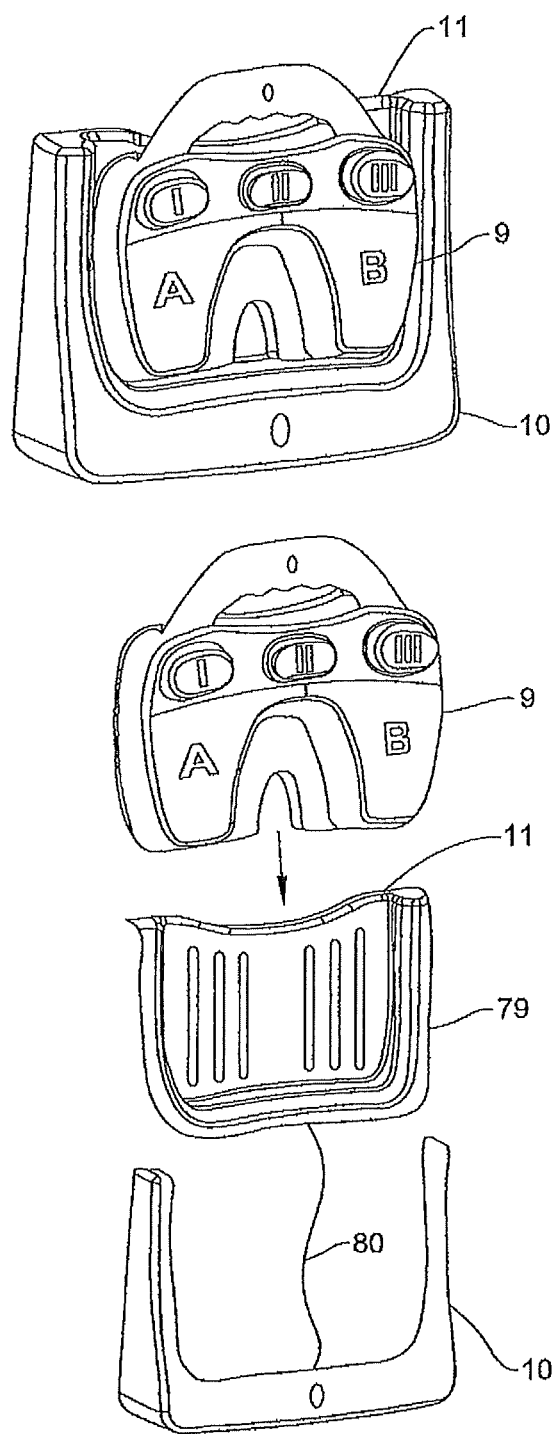
FIG. 7B shows a docking station that has a retractable charging unit.

The docking station 10 (or a combined receiver unit/docking station) may include a retractable charging unit 79, as shown in FIG. 7B. The retractable charging unit 79 allows the console 9 to be powered from the docking station 10, rather than from the console's own internal battery 54. This approach allows the console 9 to operate in the event of a battery failure and also allows the battery 54 in the console 9 to be charged from the docking station 10 while the console 9 is in use. The retractable charging unit 79 is removably attached to the rest of the docking station 10 through a retractable extension cord 80 (e.g., under spring-loaded tension). In this embodiment, the detachable charging unit 79 comprises a receptacle 11 such as described above to physically receive the console 9 and also contains the primary-side induction coil 56 (FIG. 5) or other equivalent charging elements.

The extension cord 80 extends out of, and retracts into, the docking station 10 under spring-loaded tension. When the cord 80 is fully retracted, the retractable charging unit 79 fits into and attaches to the rest of the docking station 10. The charging unit 79 can operate in either the fully retracted position or in any position of extension, within the limits of the extension cord 80. The extension cord 80 can also be used to transport the above-described control signals between the console 9 and the docking station 10.

In a given clinical environment, multiple pairs of consoles 9 and receiver units 8 may be used in close proximity to each other. This gives rise to the risk of a receiver unit 8 responding to control signals from the wrong console 9. To prevent this from occurring, each console 9 can be assigned a unique, modifiable device identifier. Each receiver unit 8 can be configured to respond to (i.e., can be "synchronized" with) one or more specific consoles 9, based on their device identifiers. During operation, when a console 9 transmits signals representing user inputs, it transmits its preassigned device identifier with those signals. The receiver unit 8 ignores any signals that are not accompanied by the correct device identifier (e.g., signals from an unknown or unauthorized console 9).

The identifier may be assigned by appropriately programming the microcontroller 51 in the console 9. In an embodiment in which the console 9 communicates with the receiver unit 8 using Bluetooth, for example, the device identifier may be the console's standard Bluetooth ID. Furthermore, the programmability of the microcontroller 51 in the console 9 enables modification of the device identifier of any given console 9, when desired. Consequently, a faulty console 9 can be easily replaced with another similar unit simply by reprogramming the device identifier of the replacement unit with that of the faulty unit.

In an embodiment in which Bluetooth is used for communication between the console 9 and the receiver unit 8, the receiver unit 8 may operate in a "non-discoverable" mode. Therefore, in order to synchronize a receiver unit 8 with a specific console 9 (i.e., to allow the receiver unit 8 to discover the identifier of the console 9), any of various approaches can be used. One approach is to push two of the switches (24, 25, 26) on the console 9 simultaneously, triggering the console 9 to transmit its identifier, coupled with a push of a "sync" button on the receiver unit 8. Another approach is to include an RF identifier coil or proximity sensor in both the receiver unit 8 and the console 9, using which the two devices can be triggered to synchronize by bringing them within close proximity of each other.

Figure 8A:
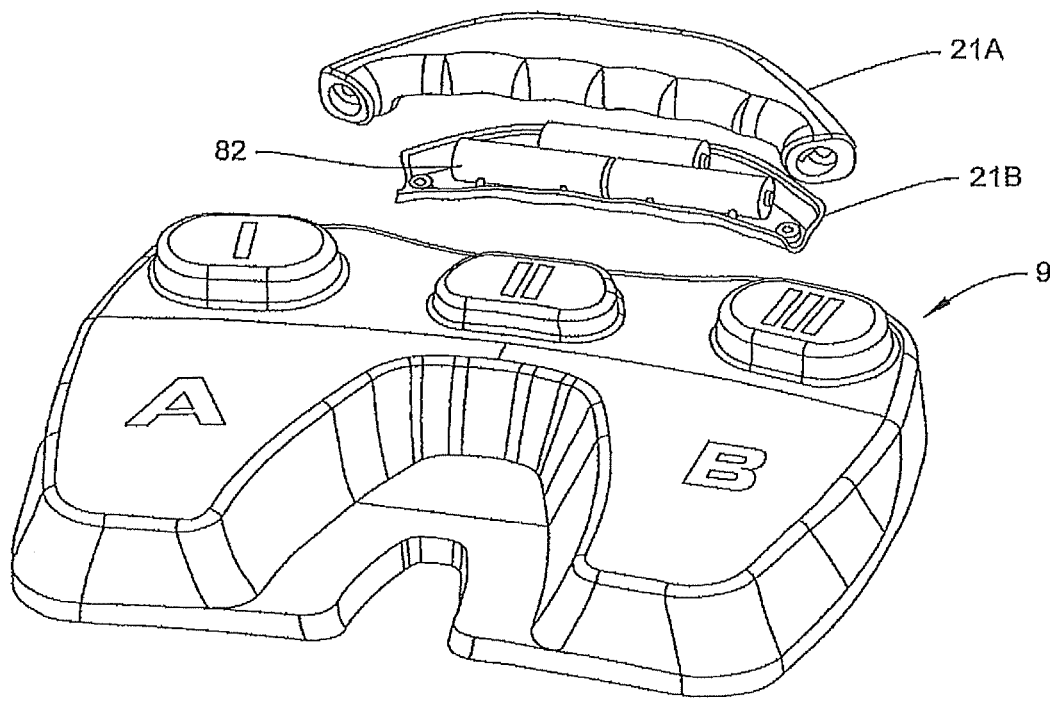
FIG. 8A shows a console with a removable handle containing batteries to power the console.

In certain embodiments, as discussed above, the console 9 is powered by one or more internal rechargeable batteries or battery pack sealed inside the housing of the console 9. For example, the battery may be sealed within the housing by a gasketed battery compartment that is externally accessible for purposes of battery service and replacement. This approach is advantageous for a variety of reasons discussed above. In one such embodiment, illustrated in FIG. 8A, the one or more batteries 82 are sealed within the handle 21, which can be removed from the console 9 and opened up into sections 21A and 21B to allow easy service and replacement of batteries 82. In this embodiment, the handle 21 is essentially a removable battery pack.

Figure 8B:
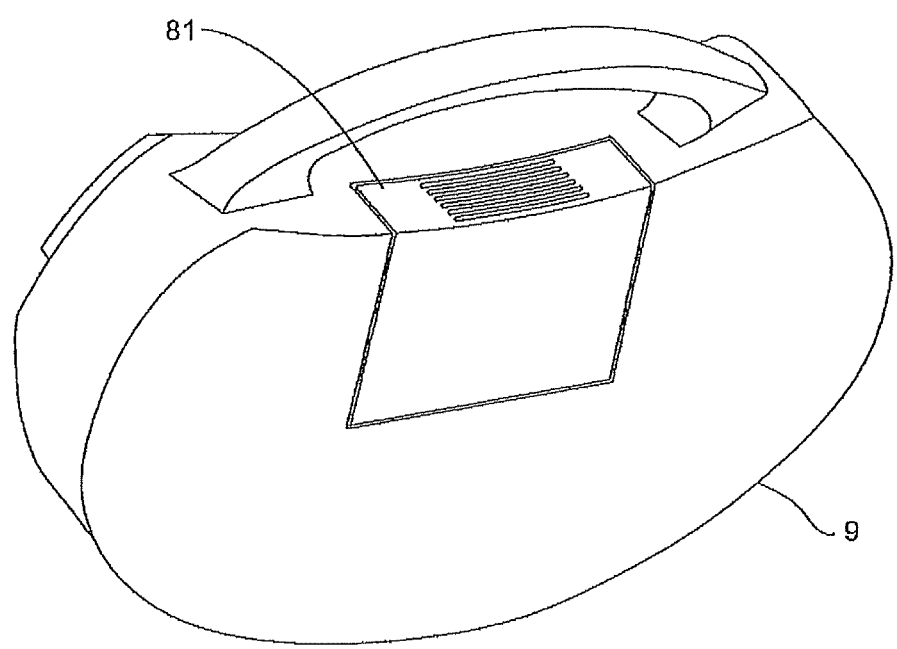
FIG. 8B shows the bottom of the console with a removable battery inserted therein.

In alternative embodiments, however, the battery is not sealed within the housing and can be removed from the console 9 and placed in a dedicated battery charger unit for recharging. In such embodiments, no docking station 10 is required. FIG. 8B illustrates such an embodiment.

Figure 9:
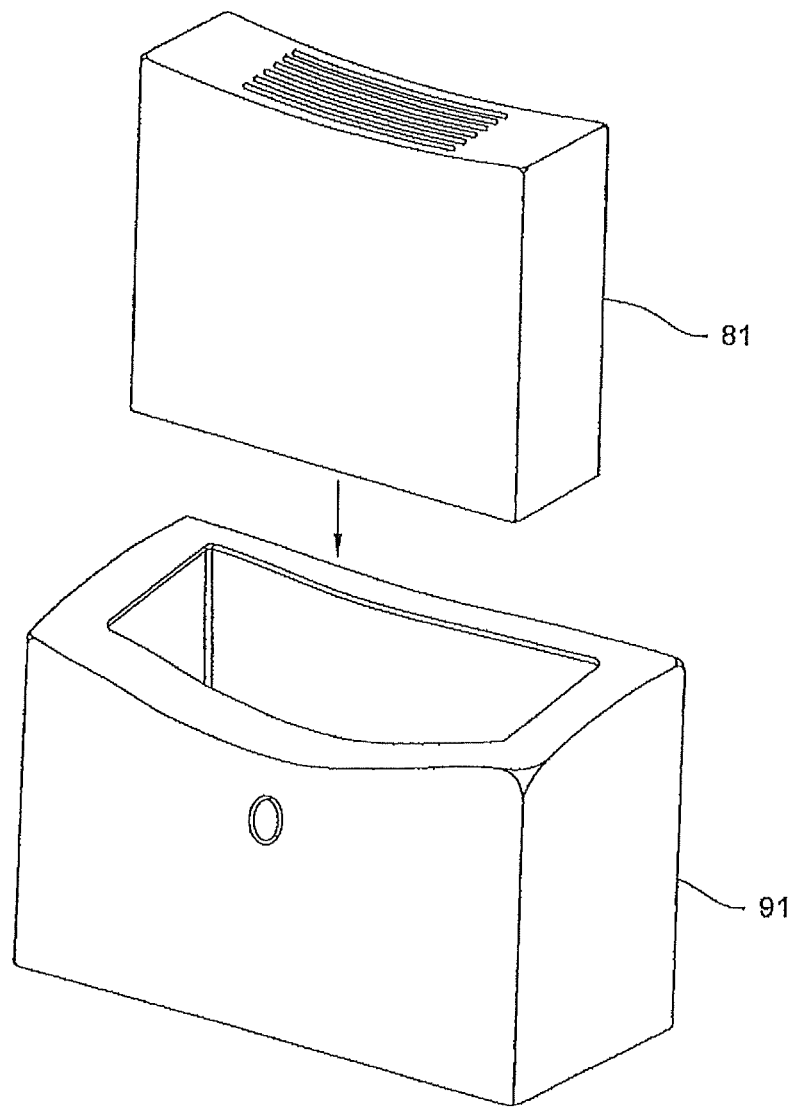
FIG. 9 shows the removable battery and a charger unit into which the battery can be inserted for recharging.
Figure 10:
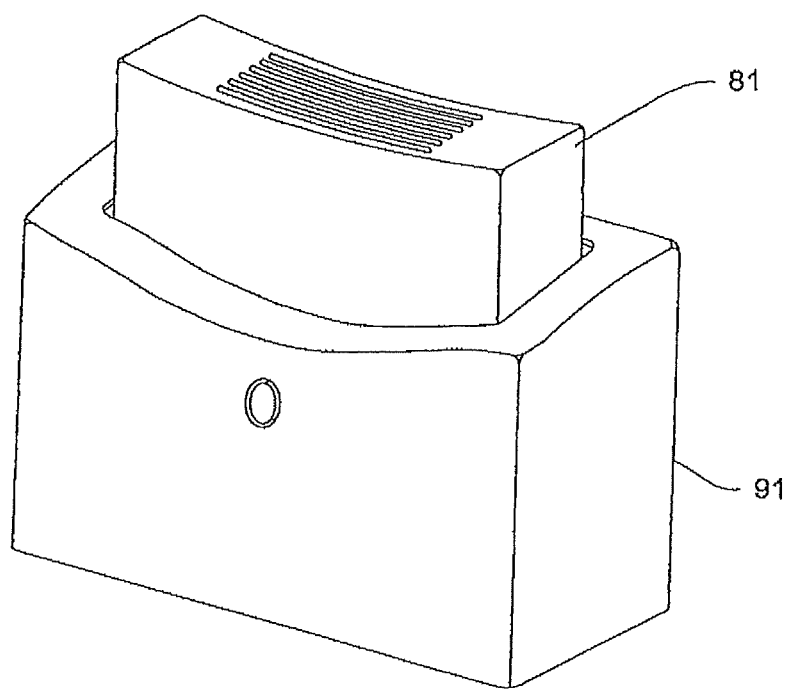
FIG. 10 shows the battery of FIG. 9 inserted into the charging unit.

Specifically, FIG. 8B shows the console 9, where a removable rechargeable battery pack 81 is inserted into a corresponding receptacle in the bottom of the console 9, to power the console 9. The battery pack 81 can be removed and placed in its own dedicated charger unit 91 for charging, as shown in FIGS. 9 and 10. FIG. 9 shows the removable battery pack 81 and a charger unit 91 into which the battery pack can be inserted for charging. FIG. 10 shows the battery pack 81 inserted into the charger unit 91.

In certain embodiments represented by FIGS. 8 through 10, the battery pack 81 itself is sealed and includes both a rechargeable battery and an inductive charging/discharging circuit. The inductive charging/discharging circuit in the battery pack allows the charger unit 91 to inductively charge the battery in the battery pack 81 when the battery pack 81 is in the charger unit 91 and, likewise, allows the battery to inductively power the console 9 when the battery pack 81 is installed in the console 9. This approach eliminates the need for electrical contacts to couple the battery pack 81 to the console 9 or the charger unit 91, which is advantageous in an operating environment where exposed electrical contacts are undesirable (due to the risk of electrical shock, sparks, etc.). In other embodiments represented by FIGS. 8 through 10, standard electrical contacts are used to charge and discharge the battery.

Figure 11:
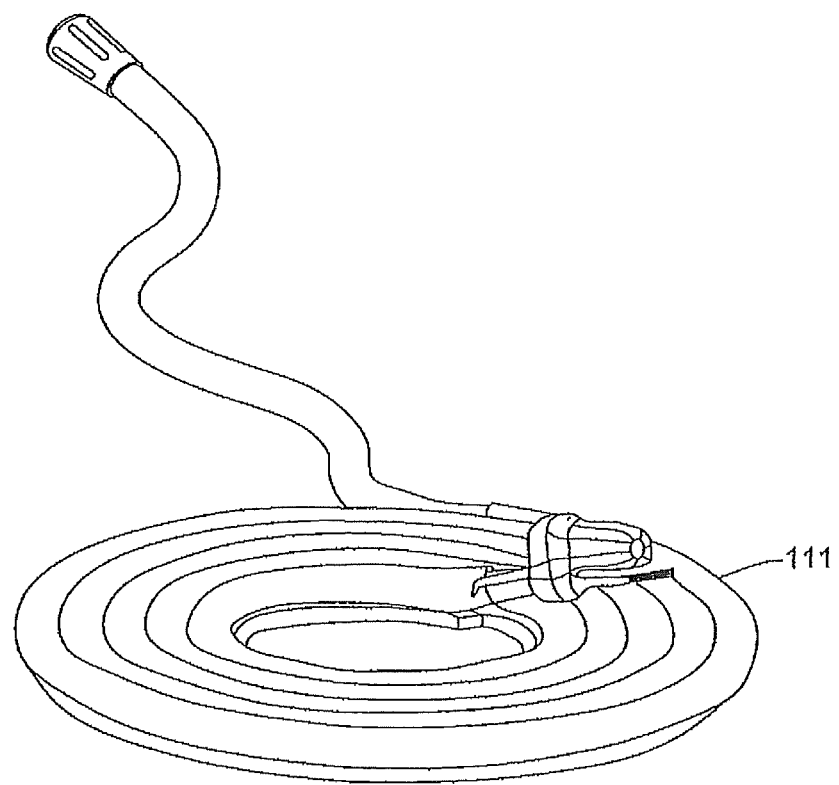
FIG. 11 shows a coiled suction hose.
Figure 12:
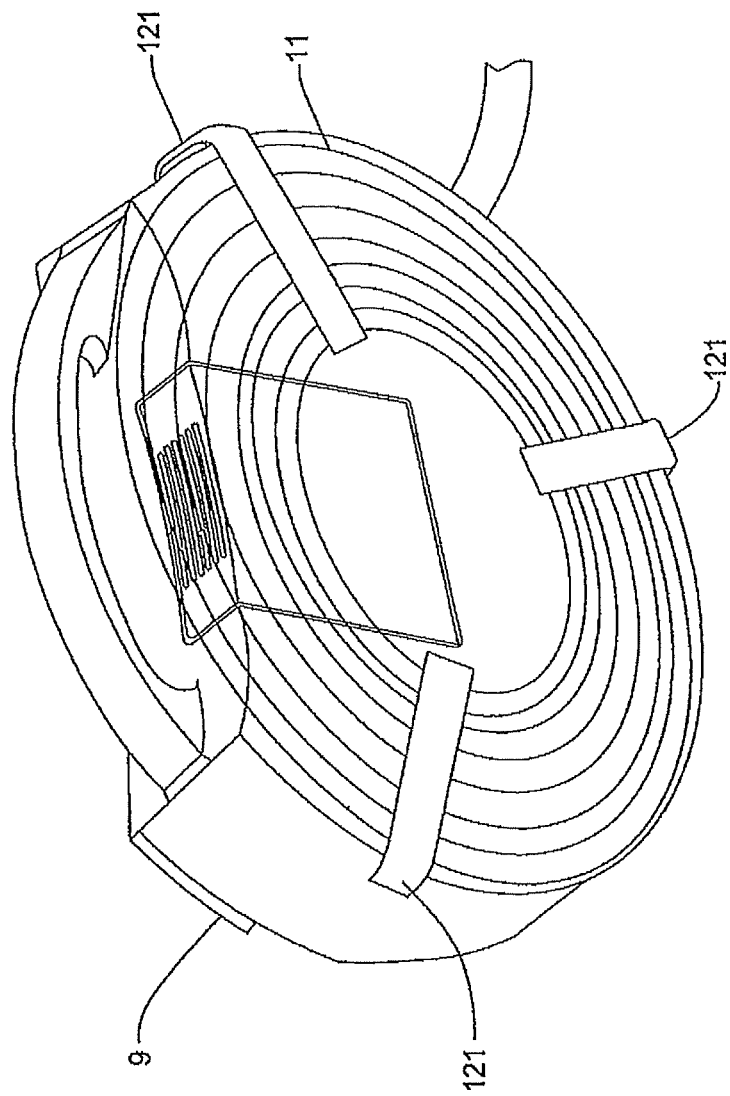
FIG. 12 shows how the suction hose can be attached to the console.

With certain endoscopic surgical procedures, it is common for significant amounts of water and/or other fluid to accumulate on the floor of the operating room. It is common during such procedures for operating room staff to place a suction hose on the floor of the operating room to remove the accumulated fluid. Therefore, the console 9 includes, in certain embodiments, a convenient attachment for a suction hose, which facilitates removal of fluids during surgical procedures. The suction hose 111 in such embodiments is permanently coiled except at its ends, as shown in FIG. 11, and includes multiple intake holes distributed along its length, to draw fluid into the hose under suction. The coiled suction hose 111 is attached to the bottom of the housing of the console 9 by clips 121 (or other fastening devices), as shown in FIG. 12, such that the console 9 can rest on top of the suction hose 111 when in use. This configuration makes it easy for operating room staff to move the console 9 and the attached suction hose 111 around on the floor with their feet to places where fluid has accumulated, in order to remove the fluid.

Figure 13:
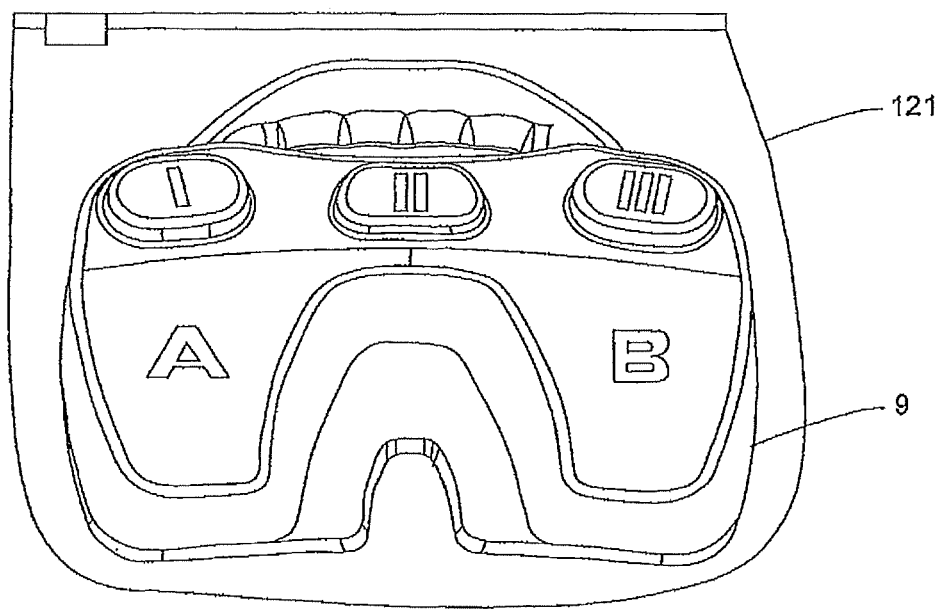
FIG. 13 shows the console contained within a protective cover.

Since the console 9 will be placed on the floor and potentially be exposed to significant amounts of water and/or other fluid, in certain embodiments the console 9 design will facilitate the attachment of a water-tight cover 121 over the console 9 in order to keep the console 9 dry, as shown in FIG. 13. In such a way, the console 9 is protected and kept clean, thus eliminating the need for time consuming cleaning steps after a surgical procedure is complete.

Thus, a wireless foot control apparatus to allow an operator to control multiple medical devices during a medical procedure has been described. Although the present invention has been described with reference to specific exemplary embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense.

We claim:

1. A foot-operated control console system to allow an operator to control a medical device during a medical procedure, the foot-operated control console system comprising:
a control console including a plurality of depressible elements, with the plurality of depressible elements including foot-operated controls designed to be operated by a foot of the operator, and at least one wireless transmitter to transmit a plurality of control signals over a wireless medium to control the medical device during the medical procedure in response to inputs from at least one of the plurality of depressible elements; and
a receiver unit for receiving the plurality of control signals from the at least one wireless transmitter, the receiver unit comprising a sync button, wherein simultaneous actuation of the sync button and at least one of the plurality of depressible elements synchronizes the control console with the receiver unit.

2. The foot-operated control console system as recited in claim 1, further comprising a controller to receive the inputs from the plurality of depressible elements and to provide the plurality of control signals to the at least one wireless transmitter.

3. The foot-operated control console system as recited in claim 1, wherein the plurality of depressible elements includes a selection control to allow the operator to select the medical device to be controlled.

4. The foot-operated control console system as recited in claim 3, wherein the receiver unit receives a selection signal based on operation of the selection control and the plurality of control signals via the wireless medium, and to control the medical device in response to the selection signal and the plurality of control signals.

5. The foot-operated control console system as recited in claim 4, wherein the receiver unit further is to control the medical device via a wired communication medium in response to the selection signal and the plurality of control signals.

6. The foot-operated control console system as recited in claim 5, wherein the receiver unit includes:
a wireless receiver to receive the selection signal and the plurality of control signals via the wireless medium;
a data communication device to transmit a plurality of controlling signals to the medical device over the wired communication medium, based on the plurality of control signals and the selection signal; and
a controller to control the data communication device in response to the plurality of control signals and the selection signal, including generating the plurality of controlling signals based on the plurality of control signals so that the plurality of controlling signals are compatible with the medical device, as indicated by the selection signal.

7. The foot-operated control console system as recited in claim 1, further comprising an internal rechargeable power source to power the control console.

8. The foot-operated control console system as recited in claim 7, further comprising:
an induction element; and
a charging circuit to control charging of the power source by power induced in the induction element by an external source.

9. The foot-operated control console system as recited in claim 1, wherein the plurality of depressible elements includes a foot pedal and a foot switch.

10. The foot-operated control console system as recited in claim 1, wherein the plurality of depressible elements includes a plurality of foot pedals and a plurality of foot switches.

11. The foot-operated control console system as recited in claim 1, wherein the control console transmits a device identifier identifying the control console in association with the plurality of control signals, the device identifier for associating the control console with the receiver unit.

12. The foot-operated control console system as recited in claim 1, further comprising a housing to contain the at least one wireless transmitter, the housing having an attachment to allow a suction hose to be attached to the housing.

13. The foot-operated control console system as recited in claim 1, wherein the simultaneous actuation of a plurality of the foot-operated controls and the sync button synchronizes the control console with the receiver unit.

14. The foot-operated control console system as recited in claim 1, wherein the plurality of depressible elements includes at least two switches for operation by the foot of the operator, a selection control for manual selection of the medical device to be controlled and a separate device control for manually operating the medical device.

15. A foot-operated control console system to allow an operator to control a medical device during a medical procedure, the foot-operated control console system comprising:
a foot-operated control console including a plurality of controls designed to be operated by a foot of the operator and at least one wireless transmitter to transmit a plurality of control signals over a wireless medium to control the medical device during the medical procedure in response to inputs from the plurality of controls; and a receiver unit for receiving the plurality of control signals from the at least one wireless transmitter;

at least one of the receiver unit and the control console including a synchronization actuator, and synchronization of the control console and the receiver unit includes depressing the synchronization actuator and at least one of the plurality of controls simultaneously.

16. The foot-operated control console system as recited in claim 15, wherein the receiver unit includes the synchronization actuator.

17. The foot-operated control console system as recited in claim 16, wherein synchronization of the control console and the receiver unit further includes depressing a plurality of the controls.

18. The foot-operated control console system as recited in claim 15, wherein synchronization of the control console and the receiver unit further includes depressing a plurality of the controls.

19. The foot-operated control console system as recited in claim 15, further comprising a controller to receive the inputs from the plurality of controls and to provide the plurality of control signals to the at least one wireless transmitter.

20. The foot-operated control console system as recited in claim 15, wherein the plurality of controls includes a selection control to allow the operator to select the medical device to be controlled.

21. The foot-operated control console system as recited in claim 20, wherein the receiver unit receives a selection signal based on operation of the selection control and the plurality of control signals via the wireless medium, and to control the medical device in response to the selection signal and the plurality of control signals.

22. The foot-operated control console system as recited in claim 21, wherein the receiver unit further is to control the medical device via a wired communication medium in response to the selection signal and the plurality of control signals.

23. The foot-operated control console system as recited in claim 22, wherein the receiver unit includes:
a wireless receiver to receive the selection signal and the plurality of control signals via the wireless medium;
a data communication device to transmit a plurality of controlling signals to the medical device over the wired communication medium, based on the plurality of control signals and the selection signal; and
a controller to control the data communication device in response to the plurality of control signals and the selection signal, including generating the plurality of controlling signals based on the plurality of control signals so that the plurality of controlling signals are compatible with the medical device, as indicated by the selection signal.

24. The foot-operated control console system as recited in claim 15, further comprising an internal rechargeable power source to power the control console.

25. The foot-operated control console system as recited in claim 24, further comprising:
an induction element; and
a charging circuit to control charging of the power source by power induced in the induction element by an external source.

26. The foot-operated control console system as recited in claim 15, wherein the plurality of controls includes a foot pedal and a foot switch.

27. The foot-operated control console system as recited in claim 15, wherein the plurality of controls includes a plurality of foot pedals and a plurality of foot switches.

28. The foot-operated control console system as recited in claim 15, wherein the control console transmits a device identifier identifying the control console in association with the plurality of control signals, the device identifier for associating the control console with the receiver unit.

29. The foot-operated control console system as recited in claim 15, further comprising a housing to contain the at least one wireless transmitter, the housing having an attachment to allow a suction hose to be attached to the housing.

30. The foot-operated control console system as recited in claim 15, wherein the simultaneous actuation of a plurality of the controls and the synchronization actuator synchronizes the foot-operated control console with the receiver unit.

31. The foot-operated control console system as recited in claim 15, wherein the plurality of controls includes at least two switches for operation by the foot of the operator, a selection control for manual selection of the medical device to be controlled and a separate device control for manually operating the medical device.

* * * * *